US00PP10987P

United States Patent [19]

Sidhu

[11] Patent Number: Plant 10,987

[45] Date of Patent: Jun. 29, 1999

[54] ***POTENTILLA FRUTICOSA* CULTIVAR NAMED 'MONSIDH'**

[76] Inventor: Gurdev Sidhu, 8653 Cedar St., Mission, British Columbia, Canada, V45-IAI

[21] Appl. No.: 08/938,278

[22] Filed: Sep. 25, 1997

[51] Int. Cl.[6] ..... A01H 5/00

[52] U.S. Cl. ..... Plt./237

[58] Field of Search ..... Plt./54.1, 237

[56] References Cited

U.S. PATENT DOCUMENTS

P.P. 4,226 3/1978 Barker ..... Plt./54

P.P. 9,321 10/1995 DeJong ..... Plt./54.1

P.P. 9,874 4/1997 Lenz ..... Plt./54.1

*Primary Examiner*—Elizabeth Kemmerer

[57] ABSTRACT

A new and distinct selection of Spring Cinquefoil which shall be referred hereinafter as *Potentilla fruticosa* cultivar Monsidh. *Potentilla fruticosa* cultivar Monsidh differs distinctively from other *Potentilla fruticosa* plants by its unique combination of a small compact dwarf habit with fine foliage and fuller growth than other whitish flower *Potentilla fruticosa.*

1 Drawing Sheet

BACKGROUND OF THE INVENTION

This invention relates to a new and distinct selection of *Potentilla fruticosa* L., native to the colder parts of the northern hemisphere and a member of the Rosaceae family. *Potentilla fruticosa* cultivar Monsidh was not a result of a controlled breeding program. The parentage of my selection is believed to be *Potentilla fruticosa* cultivar Red Ace (U.S. Plant Pat. No. 4,226) and *Potentilla fruticosa* cultivar Everest (proprietary material) as these two cultivars were in close proximity to the chance seedling. I selected this seedling believed to be a result of this cross in 1978. My discovery was made at Sidhu & Sons Nursery, 8653 Cedar Street, Mission, British Columbia, Canada. Selection was based on the attribute of small compact, dwarf habit with fine foliage and fuller growth than any other whitish flowering Potentillas I am aware of.

My new selection has been asexually reproduced by cuttings since the discovery in 1978 at Sidhu & Sons Nursery, 8653 Cedar Street, Mission, British Columbia and Monrovia Nursery Company, 18331 E. Foothill Boulevard, Azusa, Calif. Had this particular seedling not been selected and propagated, this selection may have been lost to mankind. It is unlikely these particular select and favorable attributes of this plant could be conveyed to progeny through sexual reproduction in the next generation. However, through extensive propagation by rooting of the plant it has been established that the novel exceptional characteristics of this plant are stable and reliably passed on to clonal specimens through asexual reproduction.

SUMMARY OF THE INVENTION

*Potentilla fruticosa* cv. Monsidh was observed and selected as an improvement of cultivar Abbotswood though cultivar Abbotswood is not likely part of the parentage. *Potentilla fruticosa* cv. Abbotswood is the most popular white flowering Potentilla in the horticultural trade and is widely grown and used. Cultivar Abbotswood can achieve a height of 45 to 60 cm and width of 60 to 100 cm. My selection has an ultimate size of 30 cm tall and 100 cm wide. This ground hugging habit will make it desirable as a low wide spreading cover.

The flower color on cv. Abbotswood is a clear white White Group 155C to 155D and the flower size is approximately 2 cm in diameter. My selection, cultivar Monsidh has a white creamy flower color Green-White Group 157D to Yellow-Green Group 150D with a larger flower diamter of 2.6 cm. Though this 0.6 cm does not appear significant the flower is much more noticeable as it is displayed in a more flattened plane to slightly recurved and the petals on my selection are 0.9 to 1.2 cm long and approximately 1 cm wide and overlap each adjoining petal. Whereas cultivar Abbotswood flowers are not in a flattened plane and the petals measure approximately 0.9 mm long and 0.6 mm wide and display little overlapping of adjoining petals.

The foliage on my selection and cultivar Abbotswood possess the same number of leaflets and appear the same color however, foliage size is quite different. Leaflet size is smaller on my selection and ranges from 9 mm–12. mm long and 3–4 mm wide. Cultivar Abbotswood has a longer internode length and foliage measuring 13–16 mm long and 4–5 mm wide.

BRIEF DESCRIPTION OF ILLUSTRATION

The accompanying photograph shows the plant in flower. The full flower is displayed against the background of the small pinnately compound foliage.

BOTANICAL DESCRIPTION

This detailed description of *Potentilla fruticosa* cv. Monsidh is based on 3 random samples of containerized plants grown in Oregon. Measurements were recorded the later part of the month of August. Phenotypic appearance may vary under different environmental and cultural conditions. The color terminology is based on The Royal Horticultural Colour Charts.

Overall habit: Woody shrub or groundcover with dense mounding growth, deciduous.

Overall size: Mature size expected to be 30 cm tall and 100 cm wide. This growth recorded on 10 year old plant in British Columbia.

Flowers:

*Bloom season.*—Late spring to late fall.

*Arrangement.*—Terminal cymes.

*Peduncle length.*—11 mm to 14 mm.

*Number per stem.*—3 to 5 average.

*Size.*—Diameter; 2.0 to 2.6 cm. Individual petal width: 0.9 to 1.2 cm. Individual petal length: 1.0 to 1.2 cm. Stamen length: 4 to 5 mm in vertical plane above corolla at anthesis. Stamen color: Yellow Group 2A at anthesis. Stamen number: On average 20.

*Color of mature petals and flower buds.*—Green-White Group 157D to Yellow-Green Group 150D on upper and under surface.

*Flower color effects from temperature.*—No change is noted from varying climatic temperatures.

*Shape.*—Overall flower: Petals overlap the adjoining petals, each petal recurved flattening to a horizontal plane at full anthesis.

*Pistil number.*—Approximately 30 on a pubescent receptacle.

*Pistil coloration.*—Tips Greyed-Orange Group 176A, lighter at base.

*Calyx color.*—Same as leaf color.

*Calyx number.*—Ten sepals plus epicalyx persisting after flower drop.

*Calyx shape.*—Elliptic to wide elliptic.

*Fragrance.*—None noted.

Foliage:

*Arrangement.*—Alternate on stem. Odd pinnately compound on leaf. 7–5 leaflets, rarely 7 leaflets.

*Foliage size.*—Varies considerably. Numerous small leaves within central crown area of plant of 1.0 cm inclusive of petiole. These underdeveloped leaves were not recorded in measurements.

*Length.*—1.0 cm to 1.6 cm.

*Width.*—1.5 cm–2.4 cm.

*Individual leaflet length.*—9 to 12 mm.

*Individual leaflet width.*—3 to 4 mm.

*Color upper leaflets.*—Green Group 137A and B.

*Color underside leaflets.*—Yellow-Green 148B.

*Petiole length.*—0.5 to 1.0 cm.

Fruit: Not observed.

*Seasonal foliage.*—No change of foliage coloration is observed. In British Columbia the foliage begins abscission process in end of November. Generally the plant is void of foliage in early December. Cultivar 'Monsidh' produces leaves approximately 2 weeks earlier in Spring than 'Abbotswood'.

*Stem color.*—Greyed-Red Group 178B.

*Stem surface.*—Older stems bark shredding, pubescent, densely pubescent on stipule.

*Cold hardiness.*—Able to tolerate to −40° C.

*Branching habit.*—Spreading habit ultimate size to 60 cm tall and 100 cm wide.

*Intermode length.*—1.5–3 centimeters, 2 centimeters average.

*Branching angle.*—Spreading, semi-upright.

I claim:

1. A new and distinct selection of *Potentilla fruticosa* plant substantially as shown and described which differs distinctively from other *Potentilla fruticosa* plants by its unique combination of a small compact dwarf habit with fine foliage and fuller growth than any other whitish flowering *Potentilla fruticosa*.

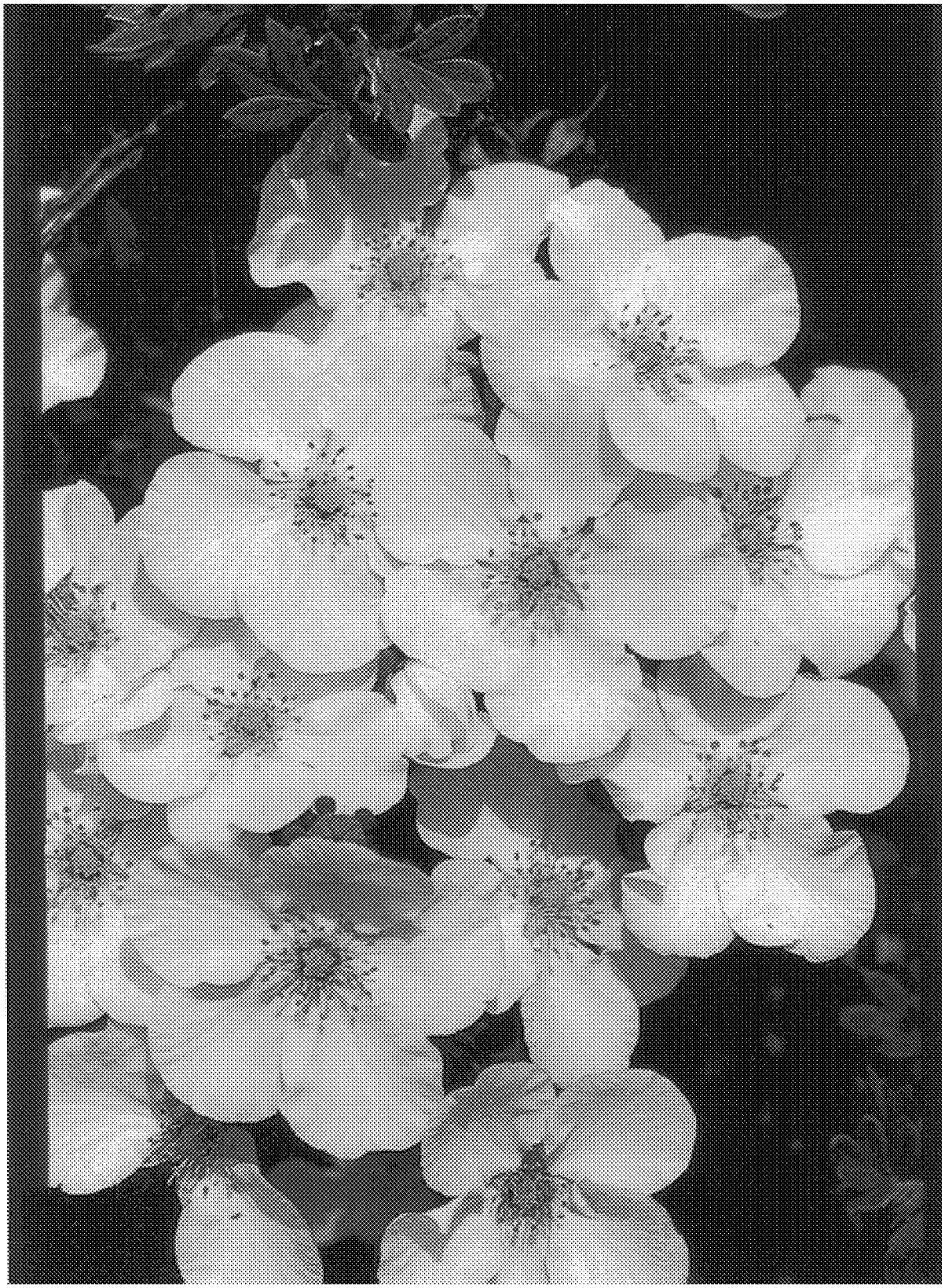

* * * * *